(12) United States Patent
Kiesel et al.

(10) Patent No.: US 9,201,000 B2
(45) Date of Patent: Dec. 1, 2015

(54) SENSOR APPARATUS AND METHOD BASED ON WAVELENGTH CENTROID DETECTION

(71) Applicant: Palo Alto Research Center Incorporated, Palo Alto, CA (US)

(72) Inventors: Peter Kiesel, Palo Alto, CA (US); Alexander Lochbaum, Moutain View, CA (US); Ajay Raghavan, Mountain View, CA (US); Bhaskar Saha, Union City, CA (US); Tobias Staudt, Palo Alto, CA (US); Lars Wilko Sommer, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 63 days.

(21) Appl. No.: 14/141,827

(22) Filed: Dec. 27, 2013

(65) Prior Publication Data
US 2015/0185139 A1    Jul. 2, 2015

(51) Int. Cl.
| G01J 3/46  | (2006.01) |
| G01N 21/27 | (2006.01) |
| G01N 21/64 | (2006.01) |
| G01N 21/77 | (2006.01) |
| G01N 21/78 | (2006.01) |

(52) U.S. Cl.
CPC .............. *G01N 21/27* (2013.01); *G01N 21/645* (2013.01); *G01N 21/77* (2013.01); *G01N 21/78* (2013.01); *G01N 21/7703* (2013.01); *G01N 2021/7753* (2013.01); *G01N 2021/7783* (2013.01); *G01N 2021/7786* (2013.01); *G01N 2021/7793* (2013.01); *G01N 2201/062* (2013.01); *G01N 2201/0612* (2013.01); *G01N 2201/08* (2013.01)

(58) Field of Classification Search
CPC ................. G01J 3/46; G01J 3/50; G01J 3/02; G01J 3/524; G01J 3/51
USPC .................................................. 356/300–445
See application file for complete search history.

(56) References Cited

U.S. PATENT DOCUMENTS

| 8,049,883 B2 | 11/2011 | Webb et al. | |
| 2008/0186503 A1* | 8/2008 | Kiesel et al. | 356/454 |
| 2009/0245317 A1* | 10/2009 | Peng et al. | 372/70 |

OTHER PUBLICATIONS

Gupta et al., "Evanescent Wave Absorption-Based Fiber Optic PH Sensor Prepared by Dye Doped Sol-Gel Immobilization Technique". Optics Communicatiions 4018 (97), pp. 30-33.
Ben-David et al., "Simple Absorption Optical Fiber PH Sensor Based on Doped Sol-Gel Cladding Material", Chem. Mater., 1997, 9, pp. 2255-2257.
Chan et al., "An Optical-Fiber-based Gas Sensor for Remote Absorption Measurement of Low-Level CH4 Gas in the Near-Infrared Region", Journal of Lightwave Technology, (3), 1984, pp. 234-237.
Sharma et al., Absorption-Based Fiber Optic Surface Plasmon Resonance Sensor: A Theoretical Evalution, Chemical 100(3), 2004, pp. 423-431.

\* cited by examiner

*Primary Examiner* — Abdullah Nur
(74) *Attorney, Agent, or Firm* — Hollingsworth Davis, LLC

(57) ABSTRACT

Sensor material is arranged to interact with input light and to asymmetrically alter a spectral distribution of the input light in response to presence of an external stimulus. A detector is configured to sense the altered input light and to generate at least one electrical signal comprising information about a shift in the centroid of a spectral distribution of the altered input light relative to a centroid of the spectral distribution of the input light.

24 Claims, 11 Drawing Sheets

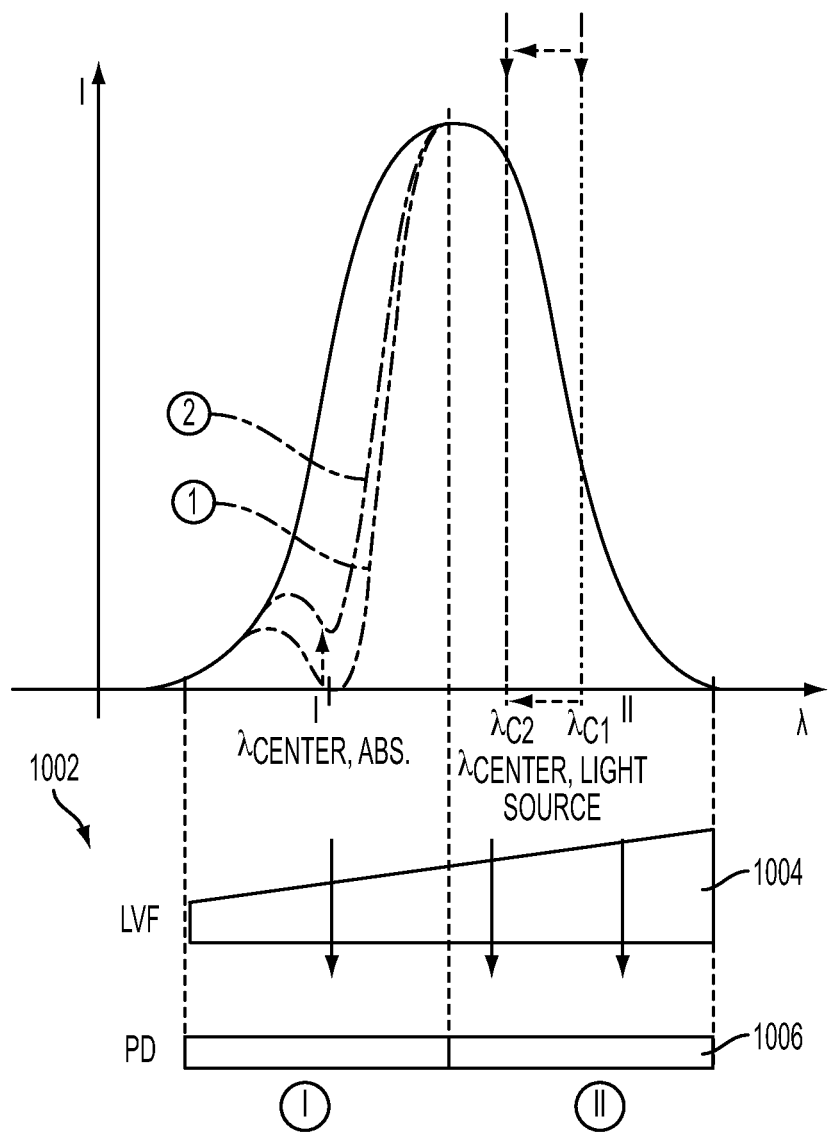

SENSOR APPARATUS AND METHOD BASED ON WAVELENGTH CENTROID DETECTION

STATEMENT REGARDING FEDERALLY SPONSORED RESEARCH AND DEVELOPMENT

This invention was made with government support under contract DE-AR0000274 awarded by ARPA-E (Advanced Research Projects Agency-Energy). The government has certain rights in the invention.

TECHNICAL FIELD

This application relates generally to detection techniques for sensing presence of an external stimulus. The application also relates to components, devices, systems, and methods pertaining to such techniques.

SUMMARY

Various embodiments of the application are directed to a system which includes sensor material arranged to interact with input light and to asymmetrically alter a spectral distribution of the input light in response to presence of an external stimulus. A detector is configured to sense the altered input light and to generate at least one electrical signal comprising information about a shift in the centroid of the spectral distribution of the altered input light relative to a centroid of the spectral distribution of the input light.

According to some embodiments, a system includes an analyte-specific sensor material arranged to interact with input light and to asymmetrically alter a spectral distribution of the input light in response to presence of a specific analyte. A detector is configured to sense the altered input light and to generate at least one electrical signal comprising information about a shift in the centroid of the spectral distribution of the altered input light relative to a centroid of the spectral distribution of the input light in response to presence of the specific analyte.

Other embodiments are directed to a method involving causing sensor material to interact with input light, such that the sensor material asymmetrically alters a spectral distribution of the input light in response to presence of an external stimulus. The method also involves sensing altered input light and generating at least one electrical signal comprising information about a shift in the centroid of the spectral distribution of the altered input light relative to a centroid of the spectral distribution of the input light.

The above summary is not intended to describe each disclosed embodiment or every implementation of the present disclosure. The figures and the detailed description below more particularly exemplify illustrative embodiments.

BRIEF DESCRIPTION OF THE DRAWINGS

FIGS. 9 and 10 show a readout apparatus in accordance with various embodiments, and further shows a sensing layer of the apparatus having an absorption spectrum which is incorporated completely into one half of the illuminating spectrum of a light source (not to scale) in accordance with various embodiments;

The figures are not necessarily to scale unless otherwise indicated. Like numbers used in the figures refer to like components. However, it will be understood that the use of a number to refer to a component in a given figure is not intended to limit the component in another figure labeled with the same number.

DESCRIPTION

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Figure 1:
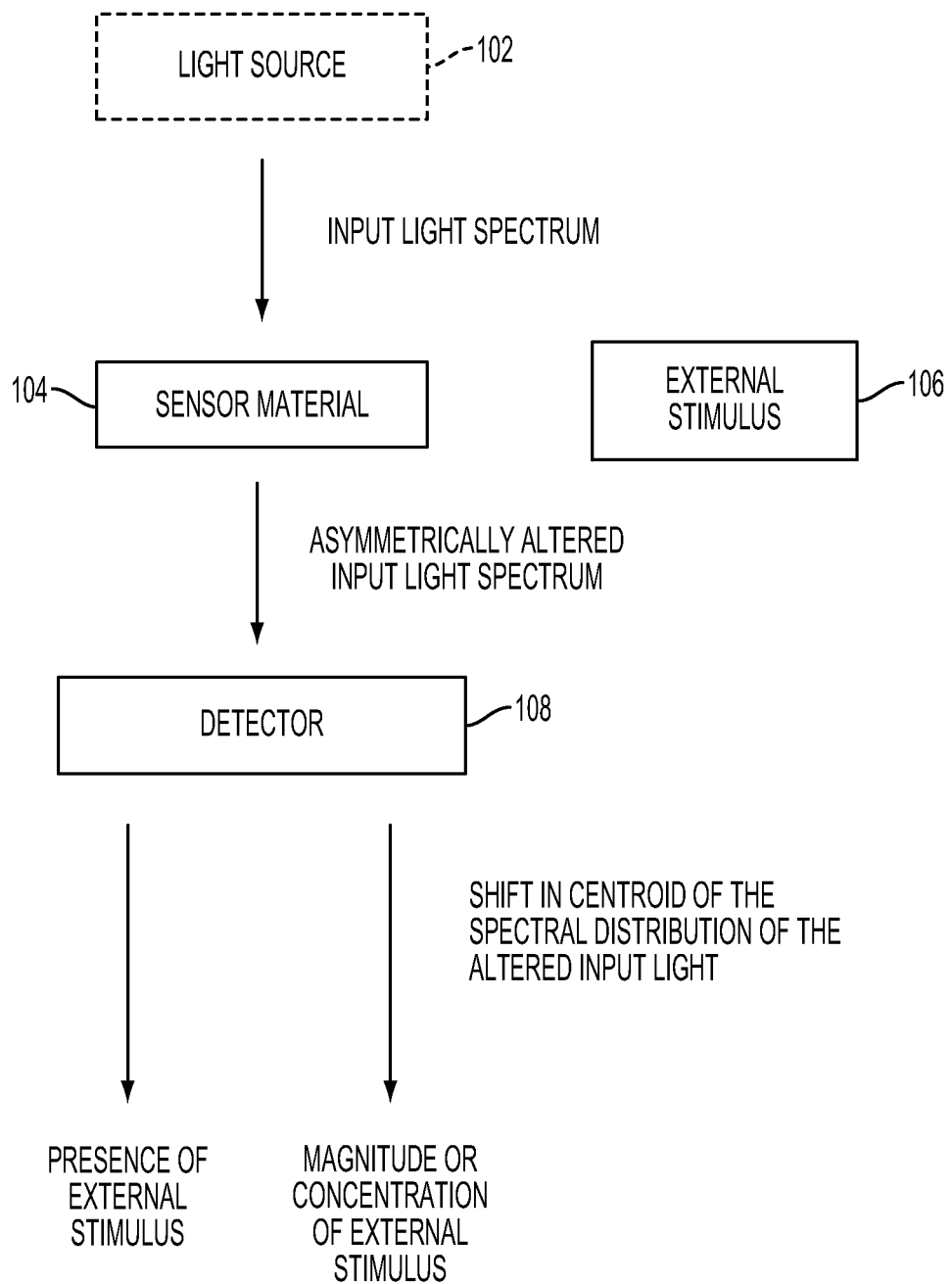
FIG. 1 shows a general block diagram of a detection apparatus according to embodiments described herein.

FIG. 1 is a block diagram of a system for detecting presence an external stimulus using an optical-based detector in accordance with various embodiments. The system shown in FIG. 1 includes sensor material 104 arranged to interact with input light, such as input light generated by a light source 102 or the sun, for example. The sensor material 104 is designed to asymmetrically alter a spectral distribution of the input light in response to presence of an external stimulus 106. The system shown in FIG. 1 further includes a detector 108 configured to sense the altered input light and to generate at least one electrical signal comprising information about a location of a centroid of a spectral distribution of the altered input light. The detector 108 is configured to directly measure a shift in the centroid of the altered input light relative to a centroid of the spectral distribution of the input light rather than determining the spectral distribution itself. The detector 108 may further be configured to determine the magnitude or concentration of the external stimulus sensed by the sensor material 104.

According to some embodiments, the sensor material 104 comprises analyte-specific sensor material. In the presence of a specific analyte, an optical property of the analyte-specific sensor material 104 changes in a specified spectral range of the input light spectrum. Representative optical properties of the analyte-specific sensor material 104 that can change in the presence of a specified analyte include absorption, transmission, scattering, light emission or reflection in the specified spectral range. A change of the optical property of the analyte-specific sensor material due to presence of the specific analyte asymmetrically alters the spectral distribution of the input light. The detector 108 is configured to determine a shift in the centroid of the altered input light relative to a centroid of the spectral distribution of the input light in response to presence of the specific analyte sensed by the sensor material 104. The detector 108 can also determine the magnitude or concentration of the analyte sensed by the sensor material 104. For example, the shift of the centroid of the spectral distribution of the input light is related to the change in analyte concentration or the change in magnitude of another form of external stimulus. After calibration and/or referencing, such as to a detector without a sensing layer, the detector 108 can directly measure the analyte concentration or stimulus amplitude. The detector 108 or an analyzer coupled to the detector 108 can include a display, which can indicate the presence of an analyte(s) or other external stimulus (or stimuli) when present, and may further display the analyte concentration or stimulus amplitude, in textual and/or graphical form.

In accordance with other embodiments, the sensor material 104 is arranged to interact with input light and asymmetrically alters a spectral distribution of the input light in response to presence of a specific electromagnetic field. In such embodiments, the sensor material 104 can include ferrofluids (e.g., $Fe_2O_3$ in octane), and measurements of filter characteristics for magnetic fields between 110 G and 280 G (11 mT-28 mT) can be conducted. In other embodiments, the sensor material 104 is arranged to interact with input light and asymmetrically alters a spectral distribution of the input light in response to presence of a specific temperature or temperature range (thermochromism). In such embodiments, the sensor material 104 can include bis(diethylammonium)tetrachlorocuprate, and the specific phase transition point is at 52-53° C., evidence by a color change from green to yellow in this illustrative example. According to further embodiments, the sensor material 104 is arranged to interact with input light and asymmetrically alters a spectral distribution of the input light in response to presence of a specific gas concentration or gas concentration range. In such embodiments, the sensor material 104 can include Binuclear Rhodium Complexes for CO detection or Bromocresol purple for $NH_3$ detection, and the specific gas concentration can be defined in the 100 ppm range for CO and 5-1000 ppm for $NH_3$, for example. The section above describes specific examples; in more general terms, the sensing layer 104 can interact and react to a large variety of external stimuli including pressure, acoustic wave; static magnetic or electric fields, and nuclear radiation, among others.

Figure 2:
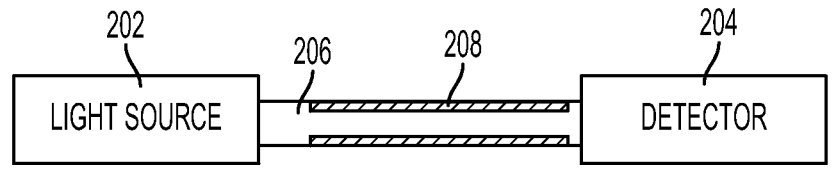
FIG. 2 illustrates a system for detecting presence of an external stimulus using an optical-based detector in accordance with some embodiments.

FIG. 2 illustrates a system for detecting presence of an external stimulus using an optical-based detector in accordance with various embodiments. In the embodiment shown in FIG. 2, the system includes a light source 202 and a detector 204 spaced away from the light source 202. The light source 202 can include a light emitting device, such as a light emitting diode (LED), a laser diode or a semiconductor laser, for example. An optical wave guide (e.g. optical fiber) 206 is disposed between the light source 202 and the detector 204. Sensor material 208 is situated in the optical wave guide 206 to interact with the guided light. In the case of an optical fiber, the whole or a part of the cladding material can be replaced by the analyte/stimulus specific sensing material.

In general, the light source 202 should be a broad band light source so that the sensing layer 208 can asymmetrically alter the spectrum. Laser sources emitting a plurality of laser modes can also be used. In the case of inelastic scattering (Raman scattering), the spectral range impacted by the sensing layer 208 can be quite narrow and, therefore, so can that of the spectral distribution of the light source (e.g., laser). As a general rule for a sensitive system, the spectral distribution of the input light should be about twice as broad as the affected spectral range of the sensing layer 208. In this case, the sensing layer 208 can most effectively asymmetrically modify the spectral distribution of the input light.

Figure 3:
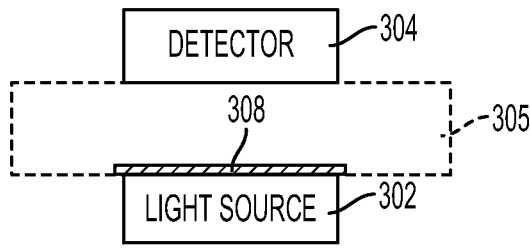
FIG. 3 illustrates a system for detecting presence of an external stimulus using an optical-based detector in accordance with other embodiments.
Figure 4:
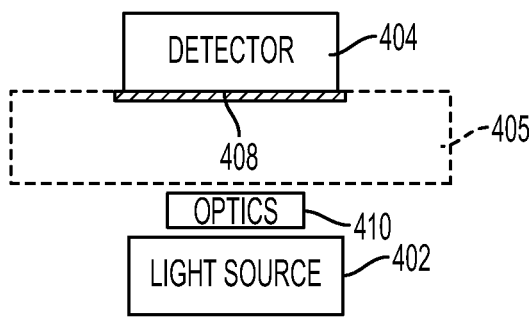
FIG. 4 illustrates a system for detecting presence of an external stimulus using an optical-based detector in accordance with further embodiments.

In the embodiment illustrated in FIG. 3, the system includes a light source 302 spaced apart from a detector 304. In the embodiment of FIG. 3, sensor material 308 is situated at the light source 302, and can completely cover the light source 302 for enhanced sensitivity. For example, the sensor material 308 can be deposited on or be in contact with the light source 302. In the representative embodiment shown in FIG. 4, the system includes a light source 402 and a detector 404 spaced away from the light source 402. According to this embodiment, sensor material 408 is situated at the detector 404, and can completely cover the detector 404 for enhanced sensitivity. The sensor material 408, for example, can be deposited on or be in contact with the detector 404. Optional optics 410 may be included within the system shown in FIG. 4 (or that shown in FIG. 3), such as between the light source 402 and the sensor material 408. In the embodiments illustrated in FIGS. 2-4, the sensor material 208, 308, 408 is arranged to interact with input light produced by the light source 202, 302, 402, respectively, and to asymmetrically alter a spectral distribution of the input light in response to presence of an external stimulus, which may be sensed within a detection region or volume 206, 305, 405.

Referring again to the embodiment illustrated in FIG. 2, the system can include an LED as a light source 202 coupled into an optical wave guide 206 which is coated with an analyte-specific coating 208 (a representative example of sensor material or a sensing layer). The sensing layer 208 has one or more optical properties that change in the presence of a specific analyte. The input light produced by the LED is preferably broad band light with a certain center wavelength and FWHM (Full-Width Half-Maximum). The presence of an analyte changes the transmission properties of the analyte-specific coating 208 on the optical wave guide 206 in a certain spectral range. Depending on the nature of the sensing layer 208, the presence of the analyte can either increase or decrease the absorption in this spectral range according to some embodiments. The sensing layer spectrum and LED spectrum are chosen so that the presence of an analyte causes a change in the spectral distribution (e.g., centroid of the spectral distribution) of the LED spectrum. In some embodiments, a wavelength centroid detector 204 is configured to measure a wavelength shift of the centroid of the spectral distribution of the altered input light (the analyte-induced changes of the LED spectrum) and to measure the analyte concentration.

According to various embodiments, the presence of an analyte causes a change in the transmitted, scattered, emitted (fluorescence) or reflected intensity of the sensing layer 208 in a certain spectral range. A change in the intensity of the sensing layer 208 impacts the spectral distribution of the incident (broad band) light source 202. The analyte concentration can be deduced from changes of a centroid of the spectral distribution (e.g., color change) of the altered input light. The center wavelength of the input light (e.g., filtered white light, LED or RC LED, broad band or multiple wavelength emission laser) and the center wavelength of the analyte-induced intensity change should not be centered. In some embodiments, a greater change in the centroid of the input light can be achieved if the analyte affects only one half of the incoming light spectrum. According to such embodiments, the sensing layer 208 is arranged to asymmetrically alter a spectral distribution of the input light in response to presence of a specific analyte, such that only one half of input light spectrum is affected by presence of the analyte.

Provided herein are several representative implementations of fiber based systems, such as systems with a coated LED or LED array. It is understood that the principles disclosed herein can be employed in many other analogous or similar implementations. Many of the representative examples provided herein use sensing layers which modify the centroid of the incoming light spectrum by creating absorption dips in the transmitted or reflected spectrum. It is understood that a sensing layer that provides for analyte-induced changes in other optical properties (elastic or inelastic light scattering, reflection, fluorescence emission, etc.) can be used to modify the spectral distribution of the incoming light. Embodiments of the disclosure provide for measuring a shift of the wavelength distribution of altered input light rather than determining the intensity at a certain wavelength (band), which is elegant and relatively simple since it does not require any wavelength referencing, thus enabling the implementation of very low cost systems.

The readout of intensity-encoded sensors, both fiber-based sensors and non-fiber-based sensors, is typically accomplished by intensity measurements, either via analyzing the optical spectrum at a certain wavelength or by illumination with a light source of certain spectral range (which spectrally overlaps with the absorption spectrum of sensing layer) and measurement of the intensity of the light after interaction with the sensing later is recorded. In order to increase sensitivity, often a second wavelength which does not spectrally overlap with the absorption spectrum is measured for reference. Examples for absorption-based fiber sensors are evanescent wave absorption-based fiber sensors. The evanescent field of the guided light in the fiber overlaps with the sensing agent directly or with a transducing material (e.g., coating, in cladding incorporated dye, etc., in general called "sensing material" in the following discussion). The propagation of the evanescent light wave through this region is connected with higher losses compared to the fiber core. Furthermore, the losses sensed by the evanescent field alter with the concentration of agent to be sensed. Hence, the intensity of the transmitted light through the fiber depends on the agent concentration.

Optical absorption-based sensors are also used in the form of non-fiber-based solutions. Excitation and detection in the infrared regime is, for example, currently used in conventional smoke detectors. Here, the intensity measurement is referenced against its own dark spectrum, i.e. if the illuminating diode is turned off in order to enable a coarse threshold measurement. To make the measurements independent of fluctuations of the light source and other distortions in the intensity of the signal, the measured intensity in the absorption band of the sensor (e.g., 570-580 nm) must be set into relation to the intensity of a band outside of the absorption range of the sensor (e.g., 910-920 nm), which spectrum is not altered by absorption of the sensing material. Thus, intensity measurements are based on the calculation of a relative intensity at two different wavelengths, respectively wavelength bands (or in other words, of an intensity ratio). Such readout schemes require either an expensive readout unit (e.g., optical spectrum analyzer) or multiple light sources and detectors (e.g., LEDs and photodiodes), which increase both complexity and cost of a readout system.

Embodiments of the present disclosure provide a readout scheme that does not depend on the evaluation of different intensities (e.g., intensity ratio) as described above, but instead detects a change in the spectral distribution of the input light due to the optical response of the sensing layer to the presence of a certain external stimulus, such as a specific analyte. Thus, there is no need to reference the measurement against another wavelength band, which makes both a second detector and a second light source obsolete. According to various embodiments, the detection methodology disclosed herein exploits the fact that the centroid of the absorption spectrum of the sensing layer is different when compared to the centroid of the input light source. In other words, the absorption spectrum of the sensing layer is placed non-centered in the illumination spectrum of the light source and thus sees a monotonic baseline.

Figure 5:
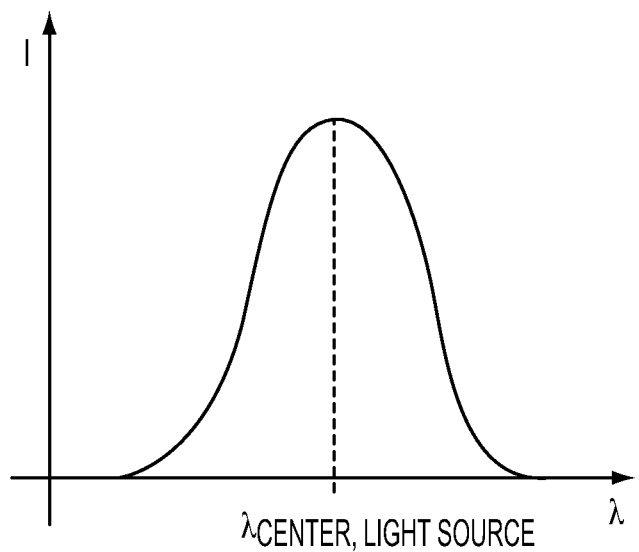
FIG. 5 shows the spectrum of a representative illuminating light source in accordance with various embodiments.
Figure 6:
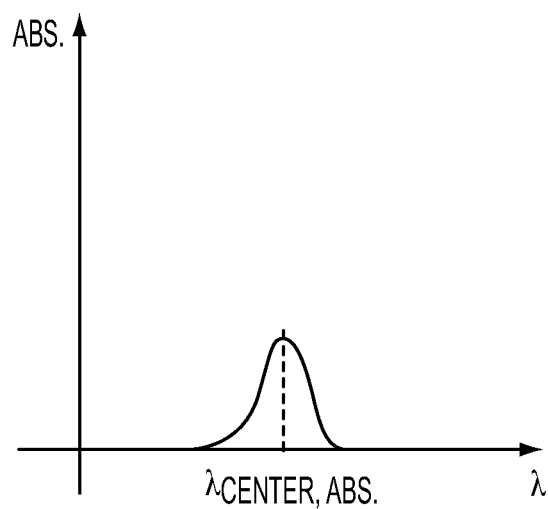
FIG. 6 shows the absorption spectrum of a sensing layer arranged to interact with input light in accordance with various embodiments.
Figure 7:
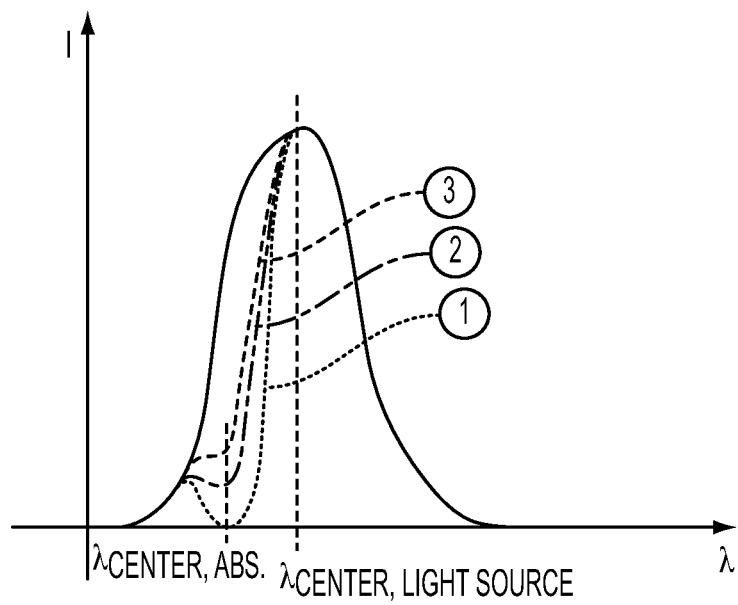
FIG. 7 shows a representative light source spectrum with a representative absorption spectrum of a sensing layer in accordance with various embodiments.

By way of example, FIG. 5 shows the spectrum of a representative illuminating light source, such as the light source illustrated in FIGS. 1-4. The illuminating light source of FIG. 5 may be a (spectrally filtered) tungsten-halogen bulb, an LED, an RC LED or a laser emitting multiple wavelengths, for example. It is understood that the spectrum shown in FIG. 5 is provided for illustrative purposes, and can look considerably different for different light sources. The representative light source spectrum shown in FIG. 5 has a center wavelength given by $\lambda_{center,Lightsource}$. FIG. 6 shows the absorption spectrum of a sensing layer, such as the sensor material shown in FIGS. 1-4. The representative absorption spectrum shown in FIG. 6 has a center wavelength given by $\lambda_{center,Abs}$. FIG. 7 shows a representative light source spectrum with a representative absorption spectrum of a sensing layer. The center wavelengths of the two spectra are labeled $\lambda_{center,Lightsource}$ and $\lambda_{center,Abs}$, respectively. For good performance, the illumination spectrum of the light source should be chosen broader than the absorption spectrum, so that the absorption spectrum can be positioned non-centered within the illumination spectrum, as is shown in FIG. 7. Hence, the centroid of the input light spectrum is different from the centroid of the illumination spectrum after interacting with the sensing layer. In FIG. 7, three different absorption levels of the sensing layer are shown respectively as broken lines 1, 2, and 3.

In accordance with various embodiments, it is important for the functionality of the detection method that the absorption spectrum of the sensing layer is placed non-centered within the illumination spectrum of the input light source. In some embodiments, the absorption spectrum can be predominantly incorporated into 'one half' of the illumination spectrum (e.g., the left side or right side relative to the center wavelength). In the illustrative embodiment of FIG. 7, it can be seen that the absorption spectrum of the sensing layer is predominantly incorporated into the left half of the illumination spectrum of the light source.

It is noted that the steeper the illumination spectrum is relative to the width of the absorption spectrum, the more sensitive the detection scheme will be with respect to changes in the absorption characteristics. However, in general, the sensing layer should only change the centroid of the illuminating light source with different analyte concentrations. Thus, the absorption spectrum could also be implemented such that it affects both sides of the illumination spectrum, as long as the centroid of the illuminating light source is altered by the sensing layer, rather than being incorporated into one side of the illumination spectrum. It is further noted that the FWHM of the absorption band can also be as broad as or even broader than the FWHM of the illumination light. In this case, the two bands should be off-centered far enough so that the absorption spectrum effectively eats away one half of the illumination spectrum. However, this configuration is less preferred since it lowers the sensitivity of the sensing system. In this case, only a portion of the absorption band of the sensing layer overlaps with the incoming light and alters its spectral distribution.

In some embodiments, rather than using a broad band illumination source, a laser emitting multiple emission wavelengths (e.g., special multi wavelengths (or broad band laser) diode) or a combination of laser diodes can be used. In such embodiments, a portion of the emission wavelengths are affected by the absorption band of the sensing layer, while another portion is not affected. This relative change in the intensity of the emission wavelengths can be measured with one wavelength centroid detector measuring the spectral shift of the centroid of the emission lines.

As previously discussed, the interaction of the light source with the sensing layer should be determined using a wavelength centroid detector which measures the centroid of the spectral input light distribution. There are many interrogation approaches that can be used for this purpose. Particularly suited for this purpose is a wavelength shift detection methodology that effectively converts the task of measuring the wavelength of the incoming light to measuring precisely the position of a light spot on a position-sensitive detector. The wavelength information is encoded into position information via a detector comprising a lateral varying coating. One useful detector, for example, is a compact and fast wavelength monitor that can resolve sub-pm wavelength changes.

Figure 8:
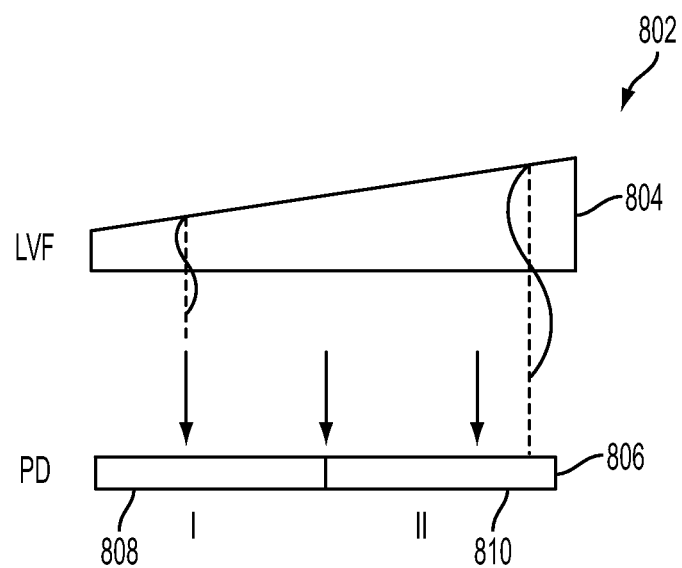
FIG. 8 shows a detector which includes a position sensitive device and a filter that cooperate to convert wavelength information of incident light into a spatial intensity distribution on the detector in accordance with various embodiments.

According to some embodiments, and with reference to FIG. 8, there is shown a detector 802 that includes a position sensing device 806 and a filter 804 (e.g., linear variable filter) that cooperate to convert the wavelength information of the incident light into a spatial intensity distribution on the position sensing device 806. Differential read-out of two adjacent elements 808 and 810 of the position sensing device 806 is used to determine the centroid of this distribution. A wavelength change of the incident light is detected as a shift of the centroid of the distribution. The detector 802 serves as a wavelength monitor, which can be used as a readout unit for any optical sensor that produces a wavelength shift in response to a stimulus.

With further reference to FIG. 8, the wavelength information of the altered input light is converted via the filter 804 into spatial information. Different filter approaches can be used, for example bandpass filters with slightly different characteristics or a linear variable filter as previously discussed. A linear variable filter 804 transmits light of a certain wavelength only at a certain position, and therefore acts as a position-dependent bandpass filter. As an example, for the linear variable filter 804 shown in FIG. 8, shorter wavelengths get transmitted on the left side, while longer wavelengths get transmitted at the right side. The transmitted light is detected by the position sensing device 806, such as a photodiode (PD), which can be split in the middle according to some embodiments, a so-called split diode. The two separated regions 808 and 810 of the split diode of position sensing device 806 can be called region I and region II, which are also shown in FIG. 8. One half of the wavelength spectrum transmitted through the filter 804 is detected by region I of the position sensing device 806, whereas the other half of the wavelength spectrum is detected by region II of the position sensing device 806.

Thus, from the resulting photocurrents of the photo detector regions 808 and 810 (which is proportional to the absorbed photons), the centroid of the light distribution in the wavelength regime can be determined, such as by taking the difference of the photocurrents from detection region I and II and dividing this difference by the sum of the photocurrents. By comparing the photocurrent produced by the adjacent detector elements 808, 810, a measure for the actual position of the centroid of the transmitted light is obtained. In order to make the read-out signal stable against intensity fluctuations, the signal can be normalized by the total incoming intensity and is typically called Differential Signal (S_Diff), which can be expressed as:

$$\text{Centroid of Light Distribution} \sim S\_Diff = \frac{I_1 - I_2}{I_1 + I_2}$$

FIGS. 9 and 10 show a readout apparatus in accordance with various embodiments. In the embodiments illustrated in FIGS. 9 and 10, the sensing layer of the apparatus 1002 has an absorption spectrum which is incorporated completely into one half of the illuminating spectrum of the light source to provide for increased sensitivity. The apparatus 1002 includes a wavelength-dependent filter 1004 (e.g., a linear variable filter or LVF) which is designed so that its full spectral range just incorporates the illumination spectrum, as is shown in FIGS. 9 and 10 (see the dashed outer lines extending between FIGS. 9 and 10). Hence, the center wavelength of the filter 1004 is the same as the center wavelength of the light source. A position sensing device 1006, according to some embodiments, includes a photodiode (PD), which can be implemented as a split photodiode (regions I and II) centered to the filter 1004. Two representative cases are highlighted in FIG. 9 (see curves 1 and 2) for purposes of illustration. It is noted that, depending on the transducing mechanism, the light source spectrum does not necessarily have to be changed in the described manner. For example, the absorption can increase with analyte concentration instead of decreasing behavior here or fluorescence can occur, for example.

In the context of FIGS. 9 and 10, the light source spectrum is altered by the absorption characteristics of the sensing layer, which may also be referred to a transducing material. The illuminating light source can be characterized by a certain FWHM and a center wavelength $\lambda_{center,Lightsource}$. The absorption characteristic of the sensing layer can be described by a certain FWHM and a center wavelength $\lambda_{center,Abs}$. As previously discussed, the filter 1004 can be a linear variable filter (LVF) and the photodiode (PD) of the position sensing device 1006 can be a split-diode with photodiode sections I and II. The detection ranges for the two photodiode sections I and II are also marked in the spectrum plot on the wavelength axis (x axis), as indicated by the dashed lines extending from the position sensing device 1006 of FIG. 10 to the wavelength axis of FIG. 9. Two different situations with different analyte concentrations are shown in spectra 1 and 2 shown in FIG. 9. In situation 1, no analyte is present; hence the absorption dip is largest and the centroid of the light source spectrum lies on the right side (labeled as $\lambda_{C1}$). If the analyte concentration increases, the absorption dip decreases, as is indicated by spectrum 2. Hence, the centroid of the light distribution on the position sensing device 1006 shifts to the left, as is indicated by a different centroid wavelength $\lambda_{C2}$, in this case. This shift of the centroid leads to a change in the photocurrent in regions I and II, and therefore changes the position sensing device output signal S_Diff, as described above. It is noted that the shift in centroid of the wavelength is exaggerated in FIG. 9 for better visualization. In a real application, the shift might be smaller. However the position sensing device 1006 described above is highly sensitive even to the slightest changes of the centroid.

Example 1

No Analyte Present

When no analyte is present, maximal absorption around the absorption center wavelength $\lambda_{center,Abs}$ occurs. The position sensing device 1006 determines the centroid of the spectral distribution by comparing the intensities on both photodiode sections I and II to each other. As significant absorption takes place in the left side of the spectrum (photodiode I), more photons get transmitted in section II (and therefore larger photocurrent gets produced in section II) and hence the centroid of the altered light source spectrum lies somewhere right of the light source center wavelength $\lambda_{center,Lightsource}$ and can be called $\lambda_{C1}$.

Example 2

Analyte Present

When an analyte specific to the sensing layer is present, absorption of the sensing layer is decreased and the absorption dip decreases slightly. In comparison to Example 1 above, more photons now get transmitted onto photodiode I and the centroid of the altered light source spectrum $\lambda_{C2}$ shifts to the left, yet still remains in the right section of the light source spectrum.

Figure 11:
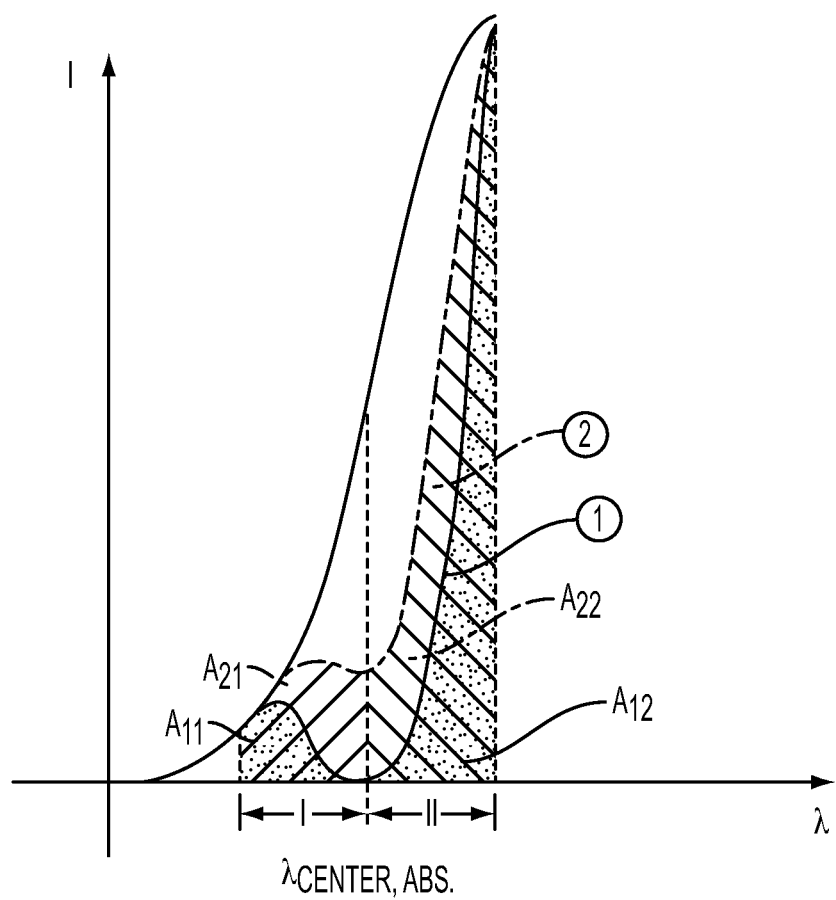
FIG. 11 shows a sensing scheme which includes a wavelength centroid detector that uses only a certain portion of the light source spectrum for determining changes to the centroid of the altered light source spectrum in accordance with various embodiments.

FIG. 11 shows another embodiment of a sensing scheme, where the wavelength centroid detector uses only a certain portion of the light source spectrum for determining changes to the centroid of the altered light source spectrum. If the detector design is tailored to the absorption band of the sensing layer, the linear variable filter transmission spectrum can be designed to be a bit broader than the absorption band of the sensor, as is indicated in FIG. 11 by the two sensing sections of the split diode labeled again as regions I and II, respectively. In FIG. 11, the characteristic absorption dip is visible with its center wavelength $\lambda_{enter,Abs}$. Curve 1 represents a situation where no sensing agent is present. Curve 2 represents a situation where sensing agent is present. The wavelength range of the linear variable filter is indicated by the two detection regions of the split diode marked by regions I and II, respectively. The detection regions I and II are sensitive to the areas below curves 1 and 2, respectively, which are labeled $A_{11}, A_{12}, A_{21}$, and $A_{22}$.

In a situation where no sensing agent is present, a dip created by the absorption of the sensing layer can be observed in the transmission spectrum, shown in FIG. 11 and labeled as curve 1. The voltage signal of detecting region I is proportional to the area $A_{11}$ below curve 1, while the voltage signal of detection region II is proportional to the area $A_{12}$ below curve 1. Hence, the centroid of the light intensity can be measured/determined accurately using the photocurrent signals generated in detection regions I and II.

If the absorption coating of the sensing material is affected by a sensing agent, the absorption coating will change its absorption characteristics. This situation is depicted in FIG. 11 as curve 2. In particular, with increasing concentration of the sensing agent, the absorption dip will become smaller, as can be seen by comparing curve 2 and curve 1 in FIG. 11. The photocurrent generated in detection region I is still proportional to the left area under curve 2, now called $A_{21}$. In the same manner, the photocurrent signal in detection region II is still proportional to the right area under curve 2, now called $A_{21}$. As can be seen in FIG. 11, due to the monotonically rising/falling illumination spectrum, the normalized changes in area between $A_{11}$ to $A_{21}$ and $A_{12}$ to $A_{22}$ are not the same. Expressed mathematically, $$\frac{A_{12} - A_{11}}{A_{12} + A_{11}} \neq \frac{A_{22} - A_{21}}{A_{22} + A_{21}}.$$

Figure 12:
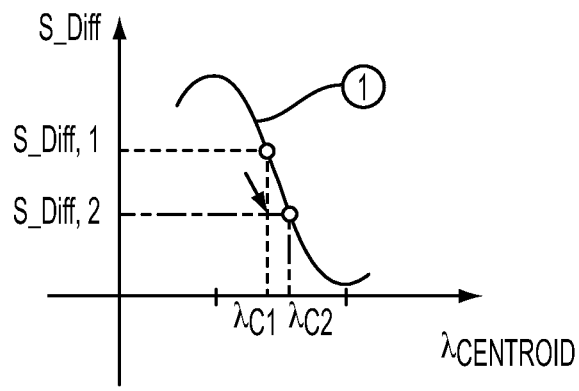
FIG. 12 shows a sensing characteristic of an example sensing layer and representative differential output signals of a wavelength centroid detector in accordance with various embodiments.

FIG. 12 illustrates the sensing characteristic, labeled curve 1, and representative output signals S_Diff_1 and S_Diff_2 of a wavelength centroid detector according to the centroid wavelengths $\lambda_{C1}$ and $\lambda_{C2}$. Due to the detector characteristic shown in FIG. 12, indicated by curve 1, a change in the centroid in the wavelength $\lambda_C$ domain (e.g., from $\lambda_{C1}$ to $\lambda_{C2}$) results in a change in the detector output signal S_Diff. Thus, it is possible to detect a change in the sensor signal when the absorption of the sensing material changes and hence it is possible to read out the intensity encoded sensor using the disclosed sensing principle with high accuracy.

A sensor apparatus according to various embodiments can include a light source, an analyte-sensitive coating (sensing layer), a linear variable filter, and a photodiode implemented or deposited together on the same substrate. In some embodiments, the analyte-sensitive coating can be deployed on top of an light source, such as an LED, RC LED or laser chip with multiple emission wavelengths. A wavelength centroid detector is situated at the other end of the optical path. Alternatively, the sensing layer can also be placed somewhere between the light source and the detector or directly deposited onto the wavelength centroid detector. It is understood that many different configurations for the integration of the readout apparatus can be chosen. For example, embodiments using face-to-face integration via flip-chip mounting or in-plane integration can be realized. Some embodiments may have optical components added in the optical path in order to increase the interaction of the light with the sensing layer or/and to increase the light collection on the wavelength centroid detector. Also, various deposition techniques can be used to grow a light source and a detection unit next to each other on the same chip or substrate.

Figure 13:
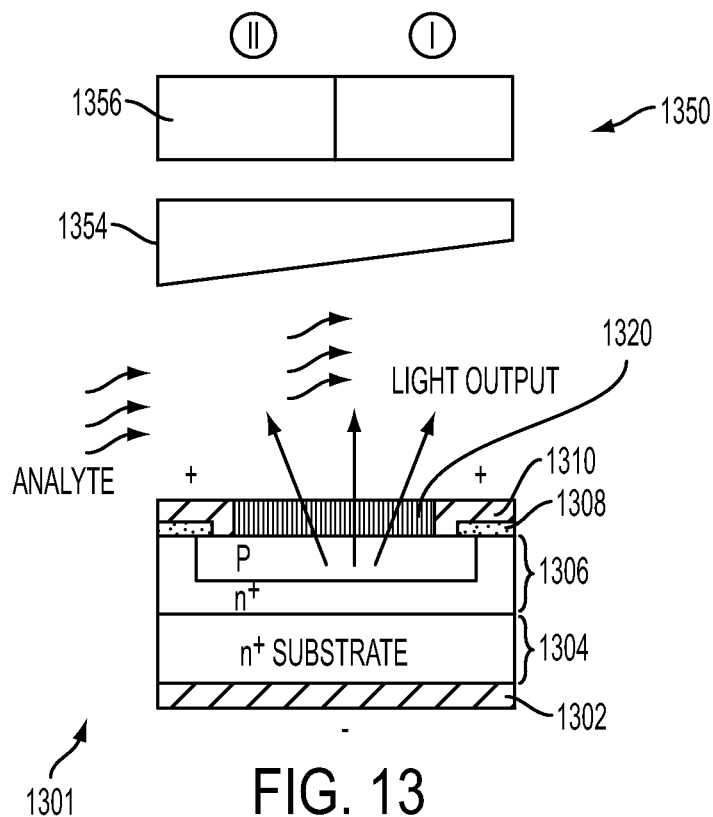
FIG. 13 is a cross-sectional view of an integrated sensor structure in accordance with various embodiments.

FIG. 13 is a cross-sectional view of an integrated sensor structure in accordance with various embodiments. The integrated sensor structure includes an external stimulus or analyte-sensitive layer 1320 deposited onto an LED structure 1301. The LED structure 1301 includes a substrate 1304 (e.g., $n^+$ substrate), an epitaxial layer 1306 ($n^+$/p layers), insulator/oxide 1308, and a contact layer 1310. Light generated by the LED structure 1301 passes through the sensing layer 1320 and is received by a wavelength centroid detector 1350. The wavelength centroid detector 1350 measures any analyte induced changes of the emitted LED spectrum, and can be placed at the other side of an analyte chamber according to some embodiments. In FIG. 13, the representative wavelength centroid detector 1350 includes a split diode photodetector 1356 covered with a linear variable filter 1354. In some embodiments, the sensing layer 1320 can be deposited onto the wavelength centroid detector 1350. In some embodiments, the sensor structure shown in FIG. 13 can be integrated into a dense sensing enclosure as an integrated unit.

Various embodiments provide for a high degree of integration and scalability that reduces response time of the entire sensing apparatus. The use of high integration fabrication techniques makes it easy to implement large arrays of sensors which allows for increasing the detection reliability (e.g., redundant sensor pixels), the realization of multiplexed sensors (different pixels are sensitive to different analytes) or for increasing the dynamic range of the sensor (e.g., by choosing an array of sensors sensitive for the same analyte but sensitive to different ranges of concentration). By using different analyte-specific coatings for each pixel, for example, the sensor can provide for multiplexed analyte detection (see e.g., FIGS. 14, 15, 18). A large variety of coatings can lead to very specific detection even if each individual sensing layer is only "weakly" specific. This is typically achieved by employing certain evaluation techniques like principal components analysis, which searches for a characteristic detection pattern.

Figure 14:
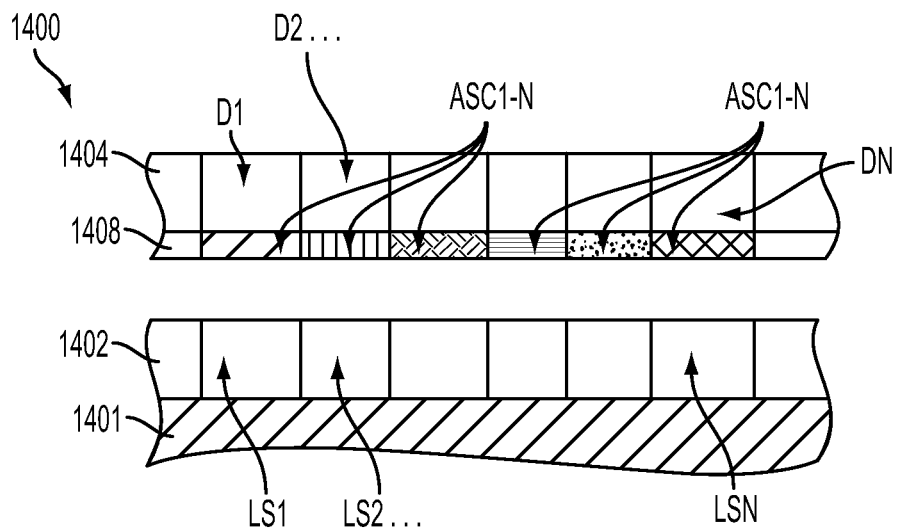
FIG. 14 shows a detection apparatus comprising an array of light sources, an array of detectors, and an array of sensing layers positioned therebetween in accordance with various embodiments.

FIG. 14 shows a detection apparatus 1400 comprising an array of light sources 1402 (LS1-LSN), an array of wavelength detectors 1404 (D1-DN), and an array of sensing layers 1408 of varying types positioned therebetween. The array of sensing layers 1408 comprises a multiplicity of sensing layers whose optical properties change in response to the presence of a specific external stimulus. For example, array of sensing layers 1408 may comprise a multiplicity of analyte-specific sensing layers (e.g., analyte-specific coatings ASC1-ASCN), each of which is sensitive to a different analyte. In the embodiments illustrated in FIG. 14, the light sources 1402 can be of various types (e.g., LED, RC LED, OLED, etc.) On the other side of the optical path, an array of wavelength detectors 1404 (which are capable of measuring the centroid of the incoming light distribution) with analyte-specific coatings 1408 is directly deposited on top of the wavelength detectors 1404 according to some embodiments. For analyte-specific detection, different coatings 1408 can be applied on each detector 1404 in order to provide specific detection on each detector 1404 for component analysis, for example. In order to increase the light sensitivity, optical components can be added between the light sources 1402 (e.g., an LED array or one or more large area LEDs facing the detector array 1404) in order to improve the photon flux.

If the wavelength centroid detector array 1404 is made sensitive to a specific wavelength band, natural illumination (e.g., sunlight or spectrally filtered sunlight to match the incoming light to the absorption spectrum of the sensing layer) may be used, and detection can involve measuring the analyte-induced changes referenced to a wavelength detector sensitive to the same wavelength band but not covered with an analyte specific sensing layer. This referencing might be needed if e.g., natural sun light is used as input light which can spectrally change during measurement. The representative examples discussed above involve intensity changes caused by an analyte-induced absorption change in a sensing layer.

Figure 16:
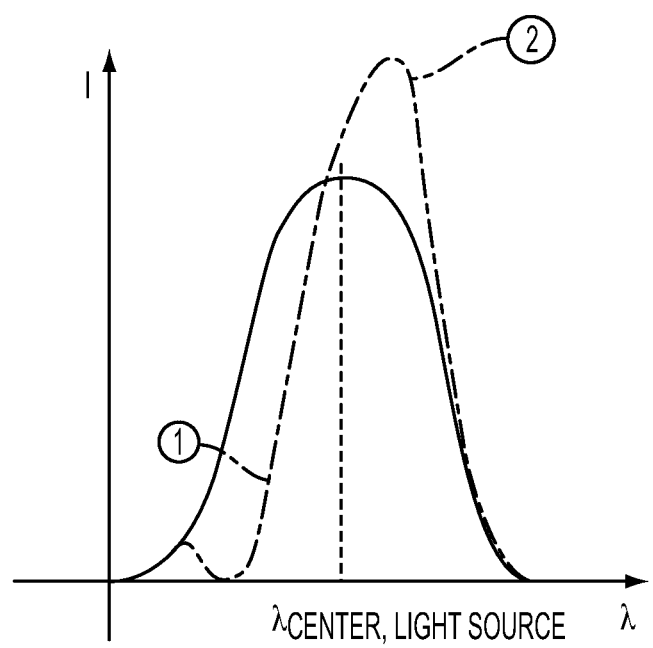
FIG. 16 shows a light source spectrum with an analyte-induced absorption dip and an analyte-induced change in the fluorescence intensity in accordance with various embodiments.

It is understood that other intensity changes can be used to sense for the presence of a specified external stimulus, such as a specific analyte. For example, analyte-induced changes in the fluorescence intensity can be employed to create changes in the centroid of the spectral distribution of light impinging on the wavelength detector (see FIG. 16). Especially sensitive are embodiments were the centroid of the input light is subject to alteration by both absorption and fluorescence emissions. In FIG. 16, the light source spectrum with analyte-induced absorption dip is labeled '1', and the analyte-induced change in the fluorescence intensity is labeled '2'. Both influences change the centroid of the altered light source spectrum.

Figure 15:
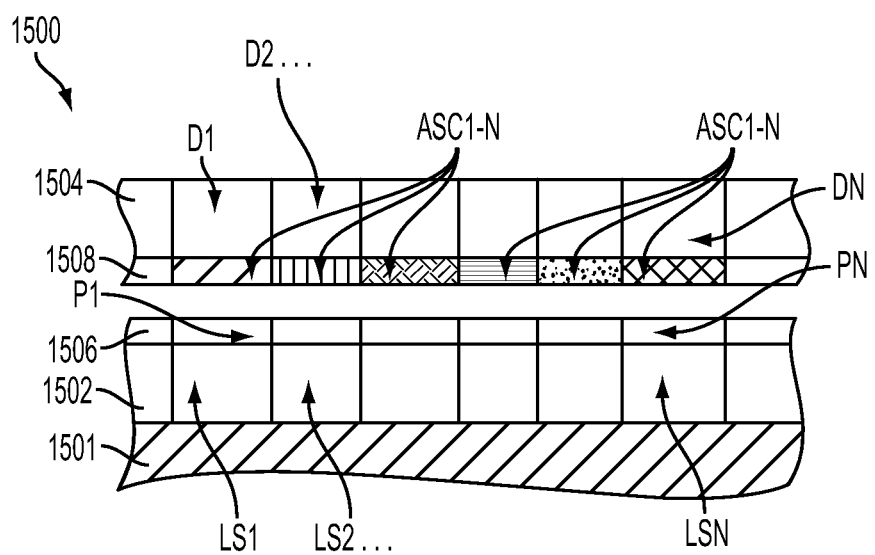
FIG. 15 shows a detection apparatus comprising an array of light sources, an array of phosphors of differing types, an array of detectors, and an array of sensing layers of varying types positioned therebetween.

FIG. 15 shows a detection apparatus 1500 comprising an array of light sources 1502 (LS1-LSN), an array of phosphors 1506 (P1-PN) of differing types, an array of detectors 1504 (D1-DN), and an array of sensing layers 1508 of varying types positioned therebetween. The array of sensing layers 1508 comprises a multiplicity of sensing layers whose optical properties (e.g., absorption and fluorescence) change in response to the presence of a specific external stimulus. For example, the array of sensing layers 1508 may comprises a multiplicity of analyte-specific sensing layers (e.g., analyte-specific coatings ASC1-ASCN), each of which is sensitive to a different analyte. Each of the sensing layers of the array 1508 requires illumination with a specified spectral range provided by an appropriate phosphor (a selected one of P1-PN) of the array 1506. Illuminating each sensing layer of the array 1508 using an appropriate phosphor of the array 1506 converts the emission spectrum of the light source 1502 to the required wavelength spectrum for each sensing layer.

In the embodiments illustrated in FIG. 15, the light sources 1502 can be of various types (e.g., LED, RC LED, OLED, etc.) The array 1502 can also include laser light sources (e.g., blue or UV laser diodes), since the phosphor array 1506 converts the laser light to the appropriate broad band light source needed as input light for the sensing layers 1508. The apparatus 1500 also includes an array of wavelength centroid detectors 1504 with analyte-specific coatings 1508 directly deposited on the detectors 1504 according to some embodiments. For analyte-specific detection, different coatings 1508 can be applied on each detector 1504 in order to provide specific detection on each detector 1504 for principal component analysis or specific pattern recognition, for example. As discussed previously, in order to increase the light sensitivity, optical components can be added between the light sources 1502 (e.g., an LED array or one or more large area LEDs facing the detector array 1504) in order to improve the photon flux.

The various examples discussed above use transmission geometry for sensing. However, many sensing concepts also work in reflection. For example, a fiber sensor with an analyte-specific coating can be used in reflection by placing a mirror at the end facet of the fiber (two pass transmission).

Such as fiber sensor may be more sensitive per fiber length since the light interacts twice with the sensing material (one time on its way to the end facet of the fiber and one time on the way back from the end facet). In a free space embodiment, for example, the sensing layer can be deposited on a mirror and the light source and wavelength detector can be arranged under 45 degree. In order to increase the sensitivity of the sensing system, the analyte-specific sensing layers can also be placed in a cavity between the input light and the wavelength centroid detector in order to increase the interaction length between input light and sensing layer.

Figure 17:
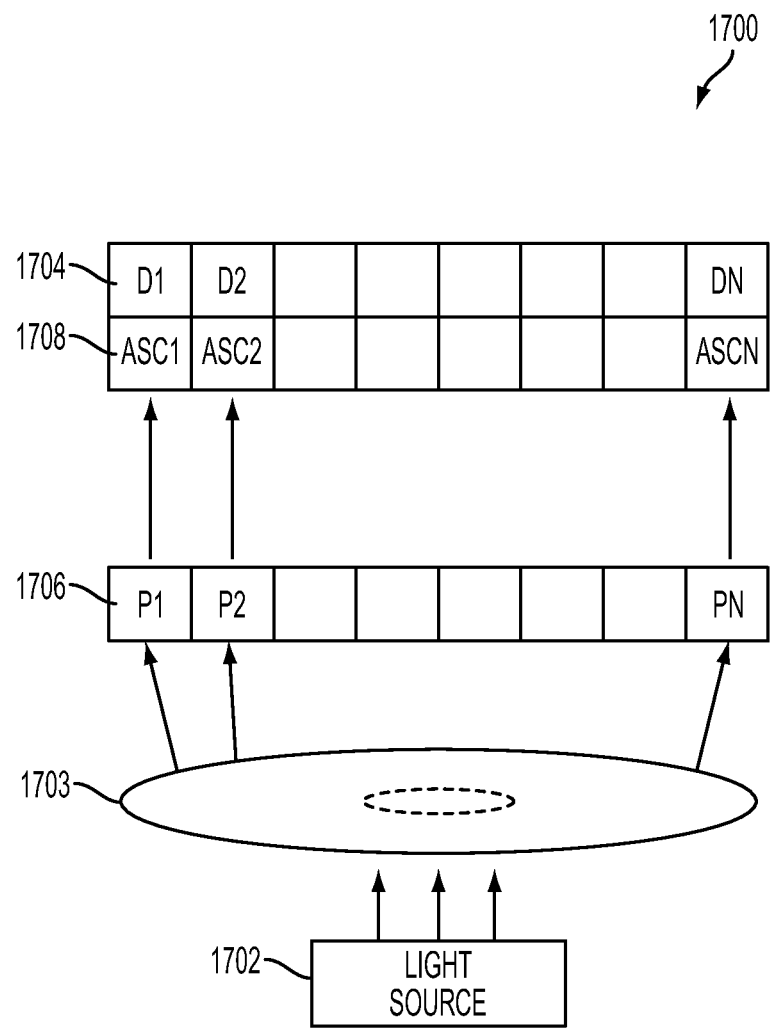
FIG. 17 illustrates a detection apparatus comprising an array of detectors, an array of phosphors of differing type, and an array of sensing layers of varying type positioned between the array of detectors and the array of phosphors in accordance with various embodiments.

FIG. 17 illustrates another embodiment of a sensing apparatus 1700 comprising an array of wavelength centroid detectors 1704, an array of phosphors 1706, and an array of sensing layers 1708 positioned between the array of detectors 1704 and the array of phosphors 1706. In the embodiment shown in FIG. 17, analyte-induced changes in absorption and fluorescence emissions can be used to detect the presence of specific analytes. The magnitude of the detected changes in centroid of the light spectrum can also be measured to determine the concentration of the specific analytes.

In the embodiment illustrated in FIG. 17, the detection apparatus 1700 includes a single light source 1702, which can be of various types (e.g., GaN LED or LD or SiC LED). In some embodiments, optics 1703 (e.g., one or more lenses) are positioned between the light source 1702 and the array of phosphors 1706. The optics 1703 direct input light produced by the light source 1702 to each cell of the phosphors array 1706 and to corresponding sensing layers 1708 and detectors 1704. In other embodiments, an array of light sources can be used, such as those shown in FIGS. 14 and 15, in which case the optics 1703 need not be included. In some embodiments, each phosphor in the array of phosphors 1706 can be shaped to act like a lens arranged to direct light from the light source 1702 towards the sensing layers 1708 and detectors 1705.

The light source 1702 (or array of light sources) and lenses 1703 (if present) are arranged to ensure that light emitted from the light source 1702 gets focused on the correct sensing layer 1708 and wavelength centroid detector 1704. Each sensing layer of the array 1708 which requires illuminations with different spectral ranges can be correctly illuminated by choosing the appropriate phosphor of the array 1706 in order to convert the emission spectrum of the light source 1702. In some embodiments, the light source 1702 can include an array of LEDs covered with phosphors 1706 providing the required wavelength spectrum for the analyte-specific sensing layers 1708. Such embodiments provide for a larger variety of sensing layers 1708 that can be combined on the same chip, even if the sensing layers 1708 are working in different spectral ranges. In some embodiments, the entire phosphor array 1706 can be supported by the same LED type. The functionalization of the different sensors (e.g., deposition of phosphors and sensing layers) can be accomplished with printing, for example.

Each of the analyte-specific sensing layers 1708 has an associated phosphor 1706. Each of the analyte-specific sensing layers 1708 has an absorption and fluorescence spectrum that is non-centered with respect to an illumination spectrum of the light source 1702. The presence of a specific analyte causes a change in absorption and fluorescence emissions of a particular analyte-specific sensing layer 1708 which can be sensed by its associated wavelength centroid detector 1704. In some embodiments, the wavelength centroid detectors of the array 1704 have analyte-specific coatings 1708 deposited directly on the detectors 1704 (e.g., to form an integrated structure). For analyte-specific detection, different coatings 1708 can be applied on each detector 1704 in order to provide specific detection on each detector 1704 for component analysis, for example. According to the embodiment of FIG. 17, analyte-induced changes in absorption and the fluorescence intensity for each sensing layer of the array of sensing layers 1708 can be employed to create changes in the centroid of the spectral distribution of light impinging on each detector of the array of wavelength centroid detectors 1704. Especially sensitive are configurations where the centroid of the light is altered by both absorption and fluorescence emissions.

Figure 18:
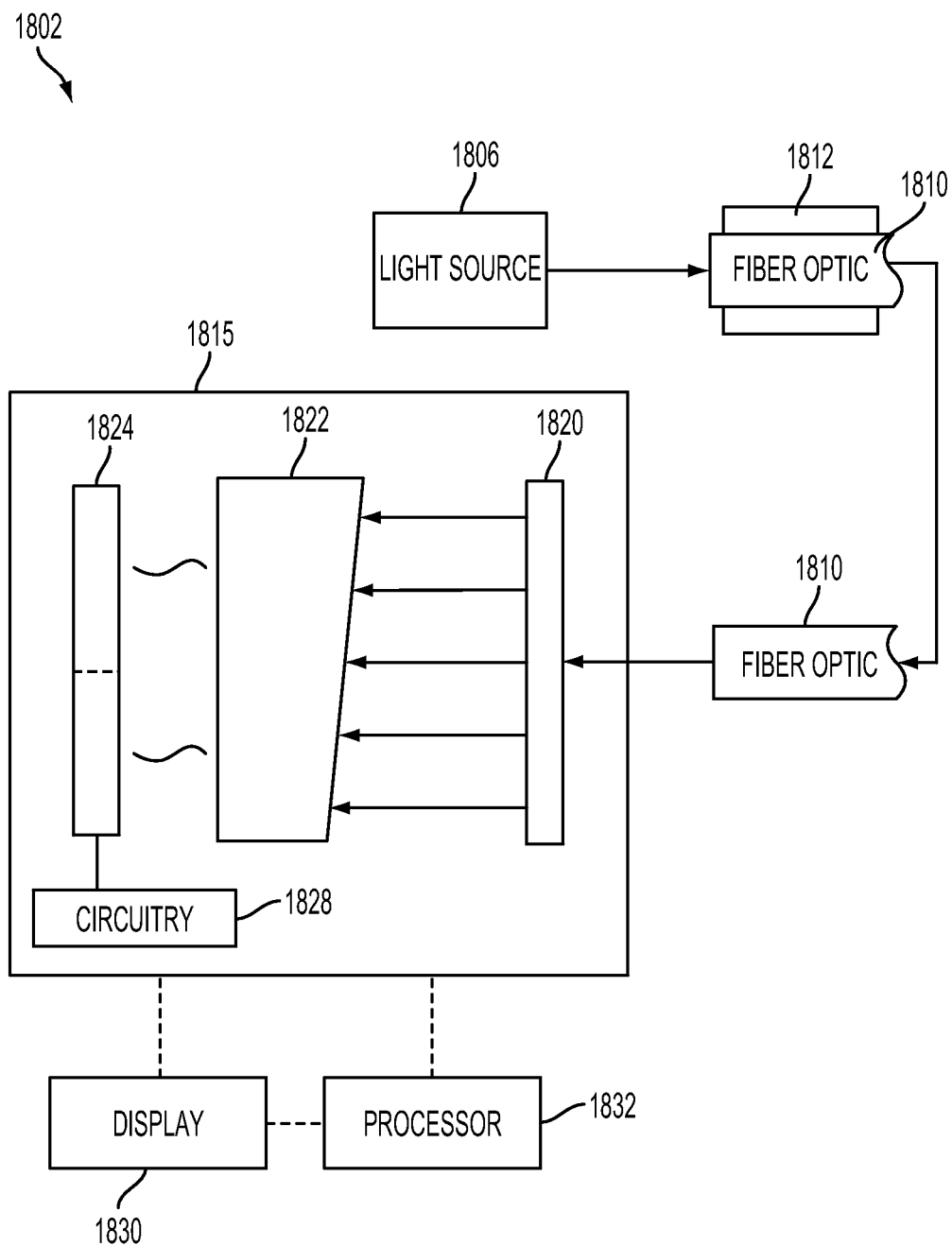
FIG. 18 is a block diagram of a detection apparatus in accordance with various embodiments.

FIG. 18 is a block diagram of a sensing apparatus 1802 in accordance with various embodiments. The apparatus 1802 includes a light source 1806 which produces input light that is coupled into an optical wave guide 1810. The optical wave guide 1810 includes a sensing layer 1812 or an array of sensing layers 1812, each of which comprises an analyte-specific material whose optical properties change in the presence of a specific analyte or stimulus. The sensing layer 1812 is arranged on the optical wave guide 1810 to interact with the input light and to asymmetrically alter a spectral distribution of the input light in response to presence of a specific analyte. The altered input light is coupled from the optical wave guide 1810 to a wavelength centroid detector 1815.

According to some embodiments, the detector 1815 includes a linear variable filter 1822 optically coupled to a photodetector 1824. The detector 1815 determines a shift in the centroid of the altered input light relative to a centroid of the spectral distribution of the input light in response to presence of the specific analyte. The detector 1815 can also be configured to determine a magnitude of the shift in the centroid of the altered input light (e.g., the concentration of the specific analyte or magnitude of the stimulus).

The photodetector 1824 is implemented as a position-dependent photo detection device according to various embodiments. In some configurations, for example, the photodetector 1824 is implemented as a split diode photodetector of a type previously described. Using the resulting photocurrents of the photodetector's split sections (e.g., regions I and II), the centroid of the light distribution in the wavelength regime can be determined by circuitry 1828 of the detector 1815. The circuitry 1828, for example, can be configured to measure the difference of the photocurrents from detection region I and II of the photodetector 1824 and divide this difference by the sum of the photocurrents, thereby providing a signal that comprises information about the actual position of the centroid of the transmitted light. In order to make the read-out signal stable against intensity fluctuations, this signal can be normalized by the circuitry 1828 using the total incoming intensity (e.g., the differential signal S_Diff, discussed previously). The detector 1815 may include an optional separator component 1820 configured to collimate and/or spread the light from the optical wave guide 1810 across an input surface of the linear variable filter 1822.

The detection apparatus 1802 may include or be coupled to an optional processor 1832 and/or a display 1830. The processor 1830 may be part of a larger system, such as an analyzer for example, and can cooperate with the detector 1815 to provide enhanced features and functionality. For example, the processor 1830 may be configured to communicatively couple to the detector 1815 for a variety of purposes, including data collection, updating programmable components of the detector 1815 (e.g., circuitry 1828), calibrating the detector 1815, and communicatively linking the detector 1815 to other devices and interfaces (e.g., an Internet interface). The optional display 1830 may be coupled directly to the detector circuitry 1828 (e.g., an input/output interface) or indirectly via the processor 1832. Data recorded by the detector 1815 can be presented on the display 1830, such as textual and graphical data.

Various embodiments of the disclosure provide for highly accurate detection of a specific analyte(s) at a relatively low cost. Some embodiments, for example, need only include one low cost light source (e.g., an LED) and one inexpensive sensor for readout. As previously discussed, sensing in another wavelength regime for compensation of source fluctuations is not required within this scheme, hence the detection scheme can be made more compact and cheaper than comparable readouts. In some embodiments, for example, the sensor used for readout is insensitive to intensity fluctuations of the incident light source and additional unwanted intensity fluctuations introduced on the optical path to the detector. Embodiments of the disclosure effectively convert an intensity-encoded sensor into a wavelength-encoded sensor with its inherent advantages.

Embodiments of the disclosed wavelength detection technique have been shown to be extremely sensitive to wavelength shifts of the centroid even for light with a relatively broad FWHM (e.g., LED). Embodiments of a readout scheme disclosed herein have been shown to be highly suitable for tracking the intensity changes within even rather broad absorption bands. Embodiments of the disclosed detection scheme have been found to be compatible with existing sensing materials and sensing apparatuses. For example, a readout scheme of the present disclosure can replace an existing detection schemes while keeping the sensor itself. A readout scheme of the present disclosure is suitable for a broad range of detection bands and adjustable also in the width of the absorption peak to be detected and tracked.

Systems, devices, or methods disclosed herein may include one or more of the features, structures, methods, or combinations thereof described herein. For example, a device or method may be implemented to include one or more of the features and/or processes described herein. It is intended that such device or method need not include all of the features and/or processes described herein, but may be implemented to include selected features and/or processes that provide useful structures and/or functionality.

In the above detailed description, numeric values and ranges are provided for various aspects of the implementations described. These values and ranges are to be treated as examples only, and are not intended to limit the scope of the claims. For example, embodiments described in this disclosure can be practiced throughout the disclosed numerical ranges. In addition, a number of materials are identified as suitable for various implementations. These materials are to be treated as exemplary, and are not intended to limit the scope of the claims.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

What is claimed is:

1. A system, comprising:
an analyte-specific sensor material arranged to interact with input light and to asymmetrically alter a spectral distribution of the input light in response to presence of a specific analyte; and
a detector configured to sense the altered input light and to generate at least one electrical signal comprising information about a shift in the centroid of a spectral distribution of the altered input light relative to a centroid of the spectral distribution of the input light in response to presence of the specific analyte.

2. The system of claim 1, wherein the analyte-specific sensor material has an absorption spectrum that is non-centered with respect to an illumination spectrum of a light source that produces the input light.

3. The system of claim 1, wherein the analyte-specific sensor material has a fluorescence spectrum that is non-centered with respect to an illumination spectrum of a light source that produces the input light.

4. The system of claim 1, wherein the analyzer is configured to determine a magnitude of the shift in the centroid of the altered input light.

5. The system of claim 1, wherein the analyte-specific sensor material is situated at the detector.

6. The system of claim 1, wherein:
the input light is produced by a light emitting device; and
the analyte-specific sensor material is situated at the light emitting device.

7. The system of claim 1, wherein:
the input light is produced by a light emitting device;
an optical wave guide is disposed between the light emitting device and the detector; and
the analyte-specific sensor material is situated on the optical wave guide.

8. The system of claim 1, further comprising:
a light emitting device arranged to provide the input light;
wherein the light emitted by the light emitting device is spectrally shifted to produce the input light.

9. The system of claim 1, further comprising:
a light emitting device arranged to provide the input light;
wherein the light emitted by the light emitting device is spectrally shifted by a phosphor to produce the input light.

10. The system of claim 1, wherein:
the analyte-specific sensor material comprises an array of analyte-specific materials arranged to interact with the input light, each of the analyte-specific materials arranged to asymmetrically alter a spectral distribution of the input light in response to presence of a specific analyte associated with each of the analyte-specific materials; and
the detector is configured to determine shifts in each of the centroids of the altered input light relative to a centroid of the spectral distribution of the input light in response to presence of the specific analytes.

11. The system of claim 10, further comprising an array of light emitting devices, each light emitting device emitting light associated with a particular analyte-specific material.

12. The system of claim 11, wherein the light emitted by each light emitting device is spectrally shifted to produce the input light for a particular analyte-specific sensor material.

13. A system, comprising:
sensor material arranged to interact with input light and to asymmetrically alter a spectral distribution of the input light in response to presence of an external stimulus; and
a detector configured to sense the altered input light and to generate at least one electrical signal comprising information about a shift in the centroid of a spectral distribution of the altered input light relative to a centroid of the spectral distribution of the input light.

14. The system of claim 13, wherein the analyzer is configured to determine a magnitude of the shift in the centroid of the altered input light.

15. The system of claim 13, wherein the sensor material has an absorption spectrum that is non-centered with respect to an illumination spectrum of a light source that produces the input light.

16. The system of claim 13, wherein the sensor material has a fluorescence spectrum that is non-centered with respect to an illumination spectrum of a light source that produces the input light.

17. The system of claim 13, wherein the detector comprises a position-dependent photo detection arrangement.

18. The system of claim 13, wherein the detector comprises a linear variable filter and a split-diode detection arrangement.

19. A method, comprising:
  causing sensor material to interact with input light, the sensor material asymmetrically altering a spectral distribution of the input light in response to presence of an external stimulus;
  sensing altered input light; and
  generating at least one electrical signal comprising information about a shift in the centroid of a spectral distribution of the altered input light relative to a centroid of the spectral distribution of the input light.

20. The method of claim 19, further comprising determining a magnitude of the shift in the centroid of the altered input light.

21. The method of claim 19, wherein the external stimulus comprises an analyte.

22. The method of claim 19, wherein the external stimulus comprises an electromagnetic field.

23. The method of claim 19, wherein the external stimulus comprises a temperature.

24. The method of claim 19, wherein the external stimulus comprises a gas concentration.

* * * * *